US012806415B2

(12) United States Patent
Raymondos

(10) Patent No.: US 12,806,415 B2
(45) Date of Patent: Nov. 24, 2026

(54) STIMULATION METHODS FOR AN ELECTROMAGNETICALLY OR ELECTRICALLY CONTROLLED SPONTANEOUS RESPIRATION

(71) Applicant: STIMIT AG, Biel (CH)

(72) Inventor: Konstantinos Raymondos, Hannover (DE)

(73) Assignee: STIMIT AG, Biel (CH)

( * ) Notice: Subject to any disclaimer, the term of this patent is extended or adjusted under 35 U.S.C. 154(b) by 234 days.

(21) Appl. No.: 18/277,336

(22) PCT Filed: Feb. 16, 2022

(86) PCT No.: PCT/EP2022/053800
§ 371 (c)(1),
(2) Date: Aug. 15, 2023

(87) PCT Pub. No.: WO2022/175317
PCT Pub. Date: Aug. 25, 2022

(65) Prior Publication Data

US 2024/0123226 A1 Apr. 18, 2024

(30) Foreign Application Priority Data

Feb. 17, 2021 (DE) ......................... 102021103734.4
Apr. 23, 2021 (DE) ......................... 102021110445.9

(51) Int. Cl.
*A61N 1/36* (2006.01)
*A61B 5/08* (2006.01)

(52) U.S. Cl.
CPC .......... *A61N 1/3601* (2013.01); *A61B 5/0816* (2013.01); *A61N 1/36031* (2017.08); *A61N 1/36034* (2017.08)

(58) Field of Classification Search
CPC .............. A61N 1/3601; A61N 1/36139; A61N 1/3611; A61N 2/006; A61N 1/36031;
(Continued)

(56) References Cited

U.S. PATENT DOCUMENTS 4,827,935 A 5/1989 Geddes et al.
5,999,855 A 12/1999 DiMarco
(Continued)

FOREIGN PATENT DOCUMENTS

DE 69918016 T2 7/2005
JP 2004136083 A 5/2004
(Continued)

OTHER PUBLICATIONS

International Search Report from corresponding International Patent Application No. PCT/EP22/53800, dated May 19, 2022.
(Continued)

*Primary Examiner* — Deborah L Malamud
(74) *Attorney, Agent, or Firm* — Renner, Otto, Boisselle, & Sklar, LLP

(57) ABSTRACT

The invention relates to an electrostimulation appliance for stimulating one or more nerves and/or muscles of a living being with electrical signals, having the following features:

a) the electrostimulation appliance has at least one signal output device through which electrical stimulation signals can be fed into at least one nerve and/or one muscle,
b) the electrostimulation appliance has at least one control device which is configured to activate the at least one signal output device in such a way that the stimulation signals output by the at least one signal output device are able to generate muscle contractions in the living being, by which the respiration of the living being can be influenced in a targeted manner.

19 Claims, 4 Drawing Sheets

(58) Field of Classification Search
CPC .................... A61N 1/3606; A61N 1/37; A61N 2005/0626; A61N 1/08; A61N 1/3629; A61N 5/0613; A61N 1/36; A61N 1/00; A61N 2/00; A61N 5/022; A61N 2005/0604; A61N 1/02
See application file for complete search history.

(56) References Cited

U.S. PATENT DOCUMENTS

| | | | |
|---|---|---|---|
| 10,406,367 | B2 | 9/2019 | Meyyappan et al. |
| 10,463,817 | B2 | 11/2019 | Li et al. |
| 10,702,445 | B2 | 7/2020 | Francois et al. |
| 11,065,443 | B2 | 7/2021 | Gelfand et al. |
| 2005/0261747 | A1 | 11/2005 | Schuler et al. |
| 2017/0304649 | A1 | 10/2017 | Sumita et al. |
| 2020/0179686 | A1 | 6/2020 | Son et al. |

FOREIGN PATENT DOCUMENTS

| | | | |
|---|---|---|---|
| JP | 2004267321 | A | 9/2004 |
| JP | 2008545516 | A | 12/2008 |
| JP | 2014512197 | A | 5/2014 |
| JP | 2015013130 | A | 1/2015 |
| JP | 2015519975 | A | 7/2015 |
| JP | 2017509465 | A | 4/2017 |
| WO | WO9738751 | A1 | 10/1997 |
| WO | 2017002917 | A1 | 1/2017 |
| WO | WO2021/123452 | A1 | 6/2021 |

OTHER PUBLICATIONS

Raymondos K, Dirks T, Quintel M, Molitoris U, Ahrens J, Dieck T, Johanning K, Henzler D, Rossaint R, Putensen C, Wrigge H, Wittich R, Ragaller M, Bein T, Beiderlinden M, Sanmann M, Rabe C, Schlechtweg J, Holler M, Frutos-Vivar F, Esteban A, Hecker H, Rosseau S, von Dossow V, Spies C, Welte T, Piepenbrock S, Weber-Carstens. Outcome of acute respiratory distress syndrome in university and non-university hospitals in Germany. Crit Care 2017; 21(1): 122.

Sander BH, Dieck T, Homrighausen F, Tschan CA, Steffens J, Raymondos K. Electromagnetic ventilation: first evaluation of a new method for artificial ventilation in humans. Muscle Nerve 2010; 42(3):305-10.

Schmidt J, Wenzel C, Spassov S, Borgmann S, Lin Z, Wollborn J, Weber J, Haberstroh J, Meckel S, Eiden S, Wirth S, Schumann S. Flow-Controlled Ventilation Attenuates Lung Injury in a Porcine Model of Acute Respiratory Distress Syndrome: A Preclinical Randomized Controlled Study. Crit Care Med 2020; 48(3):e241-e248.

Sinderby C, Navalesi P, Beck J, Skrobik Y, Comtois N, Friberg S, Gottfried SB, Lindström L. Neural Control of Mechanical Ventilation in Respiratory Failure. Nat Med 1999;5(12):1433-6.

Welvaart WN, Paul MA, Stienen GJ, van Hees HW, Loer SA, Bouwman R, Niessen H, de Man FS, Witt CC, Granzier H, Vonk-Noordegraaf A, Ottenheijm CA. Selective diaphragm muscle weakness after contractile inactivity during thoracic surgery. Ann Surg. 2011; 254(6):1044-9.

Office Action issued in related Japanese Patent Application No. 2024-501175 dated Oct. 8, 2025.

STIMULATION METHODS FOR AN ELECTROMAGNETICALLY OR ELECTRICALLY CONTROLLED SPONTANEOUS RESPIRATION

FIELD OF THE INVENTION

The invention relates to electrostimulation and, more particularly, to a device and method for stimulating one or more nerves and/or muscles of a living being with electrical signals.

BACKGROUND OF THE INVENTION

Breathing takes place to maintain gas exchange, i.e. for a life-supporting oxygen supply with simultaneous exhalation of carbon dioxide.

Depending on the nature and severity of a disease, ventilation therapy takes place with supportive to fully mechanical inhalation and a prevention of exhalation. In the event of exhaustion of the respiration pump, the respiratory muscles are relaxed during the inhalation or, in the event of gas exchange disturbances, the further loss of gas exchange surface is counteracted by prevention of exhalation. With an increasing degree of severity of the lung injury, not only is the pressure increased to prevent exhalation, the oxygen fraction during inhalation is also increased.

If, during the course of the disease, exhalation is not prevented sufficiently and in good time, very pronounced gas exchange disturbances arise in the context of extensive lung injury of ARDS (acute respiratory distress syndrome). The greatly increased respiratory work that is then needed can finally no longer be compensated by the respiratory muscles. As exhaustion increases, respiratory insufficiency develops, and breathing becomes faster and shallower. The inhalation and also the exhalation now have to be treated in combination by the ventilation.

Ventilation can support the spontaneous respiration in a synchronized manner or can take place in a controlled manner independently of the autonomous respiration. In the case of controlled ventilation, the respiratory frequency, the tidal volume or the ventilation pressure are controlled, and the breathing time ratio between inhalation and exhalation is also predefined. In addition, there are forms of ventilation which permit autonomous respiration independently of the ventilation, and numerous mixed forms. A special form of respiratory therapy is what is called high-flow oxygen therapy, in which a gas mixture is used at a high flow rate through a nasal cannula or mask.

Depending on how the airways are managed, the terms invasive or non-invasive ventilation are employed. If the airway is managed via a tracheal tube and ventilated through the latter, this is called invasive ventilation. If ventilation is carried out without a tube, this is called non-invasive ventilation or NIV. In negative-pressure ventilation, NIV can take place without airway access, whereas in the case of positive-pressure ventilation an airway access always has to be present. NIV with positive pressures can take place via a ventilation helmet or with a mask which encloses the whole face, the mouth and nose, or just the nose.

Principles of Airway Management

The airways are managed using a tube if the protective reflexes are absent, for example in the case of anaesthesia or coma. In this way, the airways are intended to be secured against aspiration, i.e. the entry of the stomach contents into the trachea, which can likewise cause ARDS. Intubation also takes place when NIV is no longer tolerated by the patient or remains unsuccessful. As soon as high ventilation pressures and high oxygen fractions are needed in the event of increasing lung injury, NIV with positive-pressure ventilation becomes unsafe and even very dangerous after a certain limit. Even the slipping of a mask, the removal of a helmet or a necessary interruption in NIV for intubation by current techniques can then lead to an inadequate gas exchange with life-threatening oxygen deficiency.

An intermediate step in airway management involves what are called supraglottic airways or SGA, such as the laryngeal mask that has been used millions of times over in anaesthesia or in emergencies. Here, no hose is inserted through the glottis into the trachea, and instead the larynx is enclosed from the outside and sealed so that ventilation can be carried out. Gastric fluid can be led away via an integrated hose at the larynx. All guidelines on airway management recommend the insertion of an SGA as soon as intubation fails and positive-pressure ventilation via the mask is also not possible. Compared to a tube within the trachea, however, the degree of airway management provided with an SGA is less, and it finds its limits at high ventilation pressures and at a high oxygen fraction. The airway may become blocked by the glottis partially or completely closing, by the roof of the larynx or by slippage of an SGA, as a result of which, particularly in the case of a high oxygen demand, the patient's life is likewise severely jeopardized.

Principles of Lung Injury

In cases of extensive lung injury or ARDS, exhalation in particular is of importance since the latter entails the following pathological changes: gas exchange surface is lost due to collapsing lung areas, since an increased permeability between blood capillaries and alveoli and/or a viral infection of the pulmonary cells means that the surface-active substance or surfactant there can no longer stabilize the alveoli during exhalation. However, blood continues to circulate through collapsed, non-ventilated lung areas, less oxygen is taken up, and, despite oxygen administration, a life-threatening lack of oxygen develops. This was recognized as early as 1967 by those who first described ARDS, and they also recognized that by providing ventilation they could counteract the collapse during exhalation. Since then, positive ventilation pressure during exhalation has been used to try to prevent the collapse of injured lung areas. This is called positive end-expiratory pressure or PEEP. The higher the PEEP, the higher the level at which the exhalation is prevented and maintained. Accordingly, the respiratory state is also shifted to inhalation, as a result of which the expiratory reserve volume (ERV) is increased and the inspiratory reserve volume (IRV) is reduced (FIGS. 3 to 5).

Current Position

Increasing invasiveness of the treatment methods resulted in more adverse effects and complications related to the treatment, so that at present the lungs, respiration and other organ systems are themselves additionally injured by the therapy itself. Furthermore, modern therapeutic measures have become more and more complicated and susceptible to error, and therefore highly specialized personnel are increasingly needed. For this reason in particular, intensive care medicine is today by far the most cost-intensive sector in the health system; in some countries, this has led to a reduction in intensive care capacity and to a reduced availability of places of treatment. Obviously, the mortality risk of ventilated patients varies considerably between different countries.

In a comparison of European countries, Germany has by far the greatest number of intensive care beds per head of population; however, the quality of care varies considerably.

Even in Germany, there are marked differences in the survival rate of ventilated patients between different levels of hospital care: In cases of extensive lung injury (ARDS), the differences are even greater, and for over 50 years now at least 50% of ARDS patients do not survive ventilation outside specialized centres. The mortality rate of ventilated patients without ARDS is at 31% in non-university hospitals, which is 50% higher than in university hospitals. In the case of ventilated patients with ARDS, it is not only the mortality rate that is twice as great in non-university hospitals but also the mortality difference by comparison with university hospitals. The independent risk of dying with ARDS is even three times as great (1).

One of the main problems is the invasive positive-pressure ventilation via the tracheal tube. Even so-called lung-protective ventilation additionally injures not only the already injured lungs and the respiratory muscles but also other organ systems. Moreover, it sets off a whole chain reaction of life-threatening complications. Mainly because of the tube, up to 50% of invasively ventilated patients additionally develop inflammation of the lungs, which causes further injury not only to the lungs but also to other organ systems. The tube in the trachea additionally activates pronounced protective reflexes, as a result of which analgosedation is required for shielding and damping. This has many side effects and results in further serious complications. Thus, overhangs often occur which prolong the duration of ventilation and therefore frequently cause ventilation-related complications. In addition, particularly in combination with positive-pressure ventilation, the sedation can considerably impair circulatory functions, so that medicaments that support the circulation have to be continuously administered. These so-called catecholamines in turn reduce blood circulation in the organs and may accelerate the failure of several organ systems. Ventilated patients with very extensive lung injury are often treated in a prone position, as a result of which they require particularly deep sedation.

Ventilation can also be carried out without a tube. However, it can then be difficult to adapt this so-called non-invasive ventilation efficiently enough to the degree of severity of the lung injury in order to avoid collapse of lung areas and increasing respiratory insufficiency. The increased respiratory drive that then occurs, with intensified and deeper breathing, then likewise causes further injury to the lungs.

SUMMARY OF THE INVENTION

Living beings control their spontaneous respiration exclusively themselves—deliberately or subconsciously. In contrast to spontaneous respiration, however, autonomous respiration can be controlled by electromagnetic or electrical stimulation. The respiratory muscles can be controlled non-invasively and in a manner free of pain, such that sufficient ventilation can be achieved via the electromagnetic stimulation (2). The phrenic nerve can also be directly stimulated via implanted electrodes. However, when performed non-invasively without implanted electrodes, electrical stimulation, in contrast to electromagnetic stimulation, from outside via the skin is painful using present-day techniques. New techniques for painless electrical stimulation are in development. Therefore, electromagnetic stimulation is hitherto the only method by which the autonomous respiration can be controlled non-invasively, painlessly and directly.

The ventilation method developed in accordance with the invention therefore represents the most natural form of non-invasive artificial ventilation. In contrast to all forms of positive-pressure but also negative-pressure ventilation, the electromagnetically controlled autonomous ventilation is the only form of ventilation with which a patient can be ventilated by natural pressure fluctuations in the chest and abdomen. With this new form of ventilation, existing conflicts between lung-protective ventilation and diaphragm-protective ventilation can be resolved, since the lungs and the diaphragm can be ventilated both effectively and gently under electromagnetic respiration. By individual control of the autonomous respiration, it is possible to avoid both inadequate and excessive respiratory efforts and the complications associated with these.

The electromagnetic or electrical ventilation can take place both in the absence and in the presence of spontaneous respiration, in these cases both independently of and in synchronization with the spontaneous respiration. By means of seven different electromagnetic or electrical stimulation patterns, divided into three groups, the autonomous respiration can be appropriately modified, controlled and/or monitored according to the disease and the respiratory disturbance.

In addition to the electromagnetic or electrical stimulation of the phrenic nerve in the neck region, stimulation can also take place at higher or more peripherally located neuronal structures. This permits targeted control of abdominal and thoracic breathing.

In accordance with aspects of the invention, a device and method for stimulating one or more nerves and/or muscles of a living being is disclosed, where such stimulation is provided with electrically, electromagnetically and/or magnetically generated stimulation signals that are fed into at least one nerve and/or one muscle of the living being. In this way, muscle contractions in the living being are generated in a targeted manner, which muscle contractions influence the respiration of the living being in a targeted manner. The method may be implemented by a computer program with program coding configured to perform such a method when the computer program is executed on a computer.

In particular, one, several or all of the following functions of the electrostimulation appliance and/or method steps are provided here.

The strength of the stimulation signals output by the at least one signal output device can be modified in several steps and/or uniformly over the course of a respiratory cycle of the living being. In this connection, further explanations are given below in the section Stimulation method 1. The stimulation signals can in this case be determined in particular with the aim of minimizing the energy input into the tissue of the lungs and diaphragm of the living being.

In order to at least partially prevent exhalation, the strength of the stimulation signals output by the at least one signal output device can be maintained at an increased level during the exhalation of the living being, at which level the muscle contraction generated by stimulation signals is greater than zero, but at least so high that up to 75% of the inspiratory reserve volume is still present in the lungs at the end of the exhalation. In this connection, further explanations are given below in the section Stimulation method 2.

By setting parameters of the stimulation signals output by the at least one signal output device, the respiration of the living being can be controlled or regulated to a predetermined value, value range and/or temporal change of the depth of respiration. In this connection, further explanations are given below in the section Stimulation method 3.

By setting parameters of the stimulation signals output by the at least one signal output device, the respiration of the living being can be controlled or regulated to a respiratory frequency of more than 40 respiratory cycles per minute. In this way, stimulation of secretion mobilization can be performed. In this connection, further explanations are given below in the section Stimulation method 4, Stimulation of secretion mobilization. In this function, it is possible in particular to control or regulate more than 60 respiratory cycles per minute. For example, 200 to 300 respiratory cycles per minute are possible with low amplitude of the muscle stimulation.

By setting parameters of the stimulation signals output by the at least one signal output device, the respiration of the living being can be controlled or regulated, for a limited time period, to a depth of respiration that is too low for a life-supporting gas exchange of the living being. In this way, a respiratory movement of the living being can also be carried out without sufficient respiration, i.e. the air volumes flowing into and flowing out of the lungs are insufficient. In this way, for example, secretion mobilization can be stimulated or training of the respiratory muscles can take place.

By setting parameters of the stimulation signals output by the at least one signal output device, complete exhalation can be prevented by shortening the duration of exhalation (duration of the expiration phase) of the living being to 0.2 to 1.3 times the duration of inhalation (duration of the inspiration phase). In addition, the strength of the stimulation signals can be increased, compared to normal respiratory cycles, in order to generate a maximum volumetric flow during the exhalation. In this way, an exhalation can be forced or accelerated, or a cough stimulation can be carried out. In this connection, further explanations are given below in the section Stimulation method 4, Cough stimulation. The duration of the inspiration phase, used as a reference for this purpose, can be for example the duration of the inspiration phase of the same respiratory cycle, or an average of the duration of several preceding inspiration phases, or a typical value of the inspiration phase duration that has been determined for the respective living being.

By setting parameters of the stimulation signals output by the at least one signal output device, the characteristics of the respiratory cycles can be controlled to predetermined target characteristics of the respiratory cycles. In this connection, further explanations are given below in the section Stimulation method 4.

By setting parameters of the stimulation signals output by the at least one signal output device, it is possible, as a function of current measured values of characteristics of the respiratory cycles of the living being which are determined continuously for example by means of at least one sensor, to regulate the characteristics of the respiratory cycles to predetermined target characteristics of the respiratory cycles. In this connection, further explanations are given below in the section Stimulation method 4.

For both of the aforementioned functions, it holds that the target characteristics can in particular be those characteristics which avoid injury to the lungs. In particular, a self-damaging breathing pattern of the living being can be avoided in this way. The control device can also be configured to limit the volumetric flow of the respiration, the respiratory movements and/or the transpulmonary pressures to a predetermined maximum value by means of the stimulation signals.

Parameters of the stimulation signals output by the at least one signal output device can be modified as a function of current measured values of spontaneous respiration impulses of the living being, in particular in a manner synchronized with the spontaneous respiration impulses. In this way, the spontaneous respiration impulse of the living being can be blocked or modified. The measured values can be determined continuously by at least one spontaneous respiration impulse sensor, which is able to detect the spontaneous respiration impulses of the living being. In this connection, further explanations are given below in the section Stimulation method 5. The spontaneous respiration impulse sensor can be designed as a nerve impulse sensor which is able to detect the nerve impulse signals of the living being that control the respiration of the living being. It is also possible, for example in the case of electromagnetic stimulation, that the signal output device for outputting the stimulation signals at the same time forms the nerve impulse sensor. For example, such a signal output device can be designed as a coil or coil arrangement. The nerve impulse can also be detected with a coil or coil arrangement.

The intra-abdominal pressure is the pressure in the abdominal cavity of the living being.

The pressure in the abdominal cavity (intra-abdominal pressure, IAP) is increased by inhalation and reduced by exhalation. Thus, in spontaneous respiration, pressure differences arise between thoracic space and abdominal space. The respiratory muscles can cause slight but also strong pressure fluctuations in the abdominal cavity. These pressure fluctuations influence the functions of the abdominal organs.

By setting parameters of the stimulation signals output by the at least one signal output device, it is possible to control or regulate the intra-abdominal pressure of the living being to a predetermined value, value range and/or temporal change. In this way, the intra-abdominal pressure can be influenced in a targeted manner. For example, the circulation of blood in certain organs can be improved by this means. For example, positive influences on the abdominal organs can be achieved. As in spontaneous respiration, the stimulation results in natural pressure differences between thoracic space and abdominal space, and natural but also strong pressure fluctuations in the abdominal cavity can also be brought about which favourably influence the functions of the abdominal organs, e.g. intestinal motility and other intestinal functions, organ blood supply or lymph drainage. This can contribute decisively to improvement of the prognosis. For example, depending on the existing intra-abdominal pressures effected by the diaphragm contractions, the depth and duration of inhalation, but also the level and duration of exhalation, can be controlled in a targeted manner.

Thus, as a function of existing intra-abdominal pressures influenced by respiration, the stimulation can control in a targeted manner the depth and the duration of the inhalation but also the level and the duration of the exhalation. If the intra-abdominal pressure, for example at an intra-abdominal hypertension (IAP>12 mbar), is so elevated that blood circulation in the abdominal organs is impaired, the stimulation can accordingly be reduced in the inhalation but also in the exhalation.

By setting parameters of the stimulation signals output by the at least one signal output device, targeted excitation of the respiratory nerves and/or the respiratory centre can be carried out. In this way, the respiratory nerves and/or the respiratory centre are activated only in a targeted manner, without this having any appreciable influence on the respiratory muscles. In particular, this does not bring about a stimulation of the respiratory muscles that is sufficient for a life-supporting gas exchange of the living being. This can be achieved, for example, if the strength of the stimulation signals is so low that almost no muscle contractions take place. In this way, the respiratory nerves and respiratory centre can nevertheless be activated and/or have their activity maintained.

Ventilation reduces the respiratory work of the respiratory muscles. The respiratory movements take place passively in ventilation; the activity of the respiratory nerves declines and may even disappear completely. This applies both to the efferent motor neurons which activate the muscles and to the afferent, sensory nerve paths which detect the extent and the speed of the muscle contraction and the corresponding change of position and report this to the respiratory centre for feedback.

In addition to the activity of the efferent and also the afferent nerve paths, the activity of the neurons in the respiratory centre in the brain stem region also decreases accordingly during ventilation. The respiratory centre reduces its activity after a ventilation time of just a few minutes. After ventilation has stopped, it is then possible to consciously activate the respiratory centre, i.e. via the cerebral cortex, but breathing is now felt to be strenuous, even though it is not. A short time after ventilation is stopped and spontaneous respiration is fully re-established in healthy living beings, a natural, autonomous spontaneous respiration then resumes, which is controlled via the respiratory centre.

With this stimulation method for activating and/or maintaining the activity of respiratory nerves and respiratory reflexes, the efferent and also the afferent neurons, i.e. the motor and sensory nerve paths with the neurons of the respiratory centre in the brain stem region, are intended to be activated and/or have their activity maintained. As in the case of conditioning, training, secretion mobilization and coughing, etc., in this stimulation method there likewise does not have to be sufficient respiration for maintaining a gas exchange.

By setting parameters of the stimulation signals output by the at least one signal output device, it is possible for the characteristics of the respiratory cycles to be controlled or regulated, over a large number of respiratory cycles, to predetermined target characteristics of the respiratory cycles, thereafter, over a large number of respiratory cycles, to have no influence on the respiratory cycles of the living being, and thereafter, again over a large number of respiratory cycles, to control or regulate the characteristics of the respiratory cycles to predetermined target characteristics of the respiratory cycles. In this connection, further explanations are given below in the section Stimulation method 6.

By setting parameters of the stimulation signals output by the at least one signal output device, it is possible, over a large number of respiratory cycles, to excite muscle contractions of the respiratory muscles of the living being which are not necessary for the gas exchange that is to be performed by the respiration of the living being and which thus produce additional muscle training. In this way, targeted muscle training of the respiratory muscles can be carried out. In this connection, further explanations are given below in the section Stimulation method 7, in particular 7.1, 7.5 and 7.6. In this kind of stimulation, the actual depth of respiration is not influenced or is influenced only with so low an amplitude that is too low for a life-supporting gas exchange of the living being. The aim of this stimulation is training of the respiratory muscles, wherein the training does not harm the organs of respiration, in particular does not harm the lung tissue and the diaphragm muscles.

By setting parameters of the stimulation signals output by the at least one signal output device, it is possible to control or regulate the respiratory state to an increased value and/or to shift the respiratory state to the inspiration phase. In this connection, further explanations are given below in the section Stimulation method 7.2.

By setting parameters of the stimulation signals output by the at least one signal output device, it is possible, on the basis of current measured values of the depth of respiration, to regulate the respiration of the living being to a predetermined value, value range and/or temporal change of the depth of respiration. For this purpose, a depth of respiration sensor can be used which continuously detects measured values of the depth of respiration of the living being. In this connection, further explanations are given below in the section Stimulation method 3 and 7.3.

By setting parameters of the stimulation signals output by the at least one signal output device, it is possible to limit the depth of respiration and/or the volumetric flow in the inspiration phase to a predetermined maximum value. In this connection, further explanations are given below in the section Stimulation method 4 and 7.4.

By setting parameters of the stimulation signals output by the at least one signal output device, it is possible to limit the volumetric flow in the expiration phase to a predetermined maximum value and/or to reduce it in relation to the average intrinsic volumetric flow of the living being in the expiration phase.

By setting parameters of the stimulation signals output by the at least one signal output device, it is possible to reduce the duration of the expiration phase in relation to the average intrinsic duration of the expiration phase of the living being. In particular, a complete exhalation of the living being can be prevented by means of the stimulation signals, i.e. at least a certain residual amount of air can be retained in the lungs.

Over the course of a respiratory cycle, the strength of the stimulation signals, output by the at least one signal output device, can be increased in the inspiration phase and reduced again in the expiration phase. In this way, the energy input into the tissue of the living being can be minimized.

A throughflow control actuator, which is coupled pneumatically and/or electrically to the respiratory system of the living being and by which the volumetric flow of the air stream flowing into and/or flowing out of the living being is adjustable, can be variably activated over the course of a respiratory cycle, in such a way that the volumetric flow in the inspiration phase and/or the expiration phase is at least temporarily limited or reduced by the throughflow control actuator. The throughflow control actuator can, for example, have an electrically actuatable valve in a breathing mask or a hose. The throughflow control actuator can be an electrical actuator with which the larynx of the living being can be stimulated, e.g. by electromagnetic laryngeal stimulation. In this way, for example during exhalation, a desired and defined resistance to the exhalation air stream can be generated, by which the airways and the alveoli are kept open.

The control device can be connectable via an interface to a ventilator which is configured to ventilate the living being by generating variable positive pressure and/or negative pressure, wherein the control device is configured for data exchange with a control device of the ventilator. This has the advantage that the control device of the electrostimulation appliance can use data, in particular measured values, which are present anyway in the ventilator, for example measured values for volumetric flow, depth of respiration and the like. Accordingly, such sensors are then not necessary in the electrostimulation appliance.

By suitably adapting the strength of the stimulation signals output by the at least one stimulation device, it is possible to initially bring about deep inhalation in the respiratory cycle. This is advantageous in the case of Stimulation method 2 for example, in order thereby to open the lungs and accordingly perform recruitment stimulation. In the case of cough stimulation, this can be advantageous, for example, in order to take up a maximum volume of air in the lungs, which promotes the cough stimulation, because a lot of air is available for generating a high volumetric flow in the exhalation.

It is possible, for example, to carry out cough stimulation if, by suitably adapting the strength of the stimulation signals output by the at least one signal output device, deep inhalation is initially brought about in the respiratory cycle, and, subsequent to the deep inhalation, and by setting parameters of the stimulation signals output by the at least one signal output device, one or more partial exhalations are brought about with, compared to the average exhalation, a shortened exhalation duration and/or an increased strength of the stimulation signals, e.g. by complete exhalation being prevented, e.g. by the exhalation duration being shortened to 0.2 to 1.3 times the inhalation duration. In addition, the strength of the stimulation signals can be increased compared to normal respiratory cycles, in order to generate a maximum volumetric flow during exhalation. It is possible in particular, subsequent to deep inhalation and by suitably adapting the strength of the stimulation signals output by the at least one signal output device, to generate several such exhalations with a shortened exhalation duration and/or a maximum volumetric flow, without an inhalation being generated in the meantime.

It is further advantageous to carry out such cough stimulation directly in time after stimulation of secretion mobilization. As has been mentioned, secretion mobilization can be stimulated by setting parameters of the stimulation signals output, by the at least one signal output device, in order to control or regulate the respiration of the living being to a respiratory frequency of more than 40 respiratory cycles per minute.

It is possible, on the basis of the output stimulation signals, to alternately stimulate purely thoracic breathing, purely abdominal breathing or a combination thereof. The strengths of the stimulation of abdominal breathing and of thoracic breathing can be adaptable independently of each other. In this way, the thoracic breathing and the abdominal breathing can be stimulated independently of each other. Thus, by increased activation in the thoracic region, with the respiratory state shifted to inhalation and with continuous prevention of exhalation, the total cross section of the diaphragm can be greatly increased throughout the respiratory cycle. In this way, independently of the thoracic breathing, respiration can now be performed much more effectively with far fewer respiratory movements and therefore with much less stress on the lungs and also the diaphragm.

Electrically, electromagnetically and/or magnetically generated stimulation signals can now be fed by the signal output device into at least one nerve and/or one muscle. The strength of the stimulation signals can be defined, for example, by the voltage or current amplitude, the electrical power, the amplitude of a magnetic variable and/or a short-term mean value of one or more such variables. For example, the signals fed into the signal output device for generating the stimulation signals can be alternating voltage or alternating current signals or other pulse-like signal sequences.

The signal output device can in principle be any desired signal output device or a combination of several signal output devices by which such electrical stimulation signals can be fed into at least one nerve and/or one muscle. Thus, by means of the signal output device, a muscle can be directly excited to contraction by electrical signals, and/or it can be excited indirectly by electrical stimulation of the corresponding nerve which can excite the muscle contraction. For example, the signal output device can have implanted electrodes which are implanted at a suitable location in the body of the living being and by which the stimulation signals are fed directly into the body.

In an advantageous embodiment, the signal output device has signal output elements which can be arranged externally on the living being and accordingly do not have to be implanted. In this way, invasive steps can be avoided. For example, the signal output elements can have one or more electrical coils by which electrical signals can be fed inductively into the at least one nerve and/or one muscle. By means of such coils, magnetic fields are fed into the living being which, within the body, in turn lead to induced currents which are able to generate the desired electrical stimulation signals in at least one nerve and/or one muscle. For this purpose, it is possible, for example, to use coils or coil arrangements according to WO 2019/154837 A1 or WO 2020/079266 A1.

The signal output elements can also comprise electrodes which are placed on the body of the living being, for example fastened to the skin, and which can galvanically couple electrical signals into the body. A further possibility is that the signal elements can have capacitive electrodes through which by means of capacitive coupling, i.e. without galvanic contact with the living being, the electrical stimulation signals can be fed into the living being.

The electrostimulation appliance can be configured to stimulate in principle any desired nerves with which the respiration of the living being can be influenced in a targeted manner. This also includes the stimulation of the muscles of respiration in the neck region, but also the stimulation of the nerve root, likewise nerves in the brain region, e.g. in the brain stem and/or in the cerebellum. For example, the electrostimulation appliance can be designed to stimulate one or more of the following nerves: phrenic nerve, one or more intercostal nerves, first, second, third motor neuron, provided these are able to trigger respiratory movements.

For the desired influence of the respiration of the living being by the stimulation signals, the signal output device or its signal output elements are designed in such a way that they can be placed appropriately and safely at the suitable position of the living being: for example, for stimulation of the diaphragm, in the region of the phrenic nerve near the head and/or, for stimulation of thoracic breathing, in the region of one or more of the intercostal nerves. For this purpose, the signal output elements are adapted, in terms of their shape and nature, to this appropriate positioning on the living being.

The control device can be configured, for example, to store characteristics of one or more breaths of a living being, by means of the control device having a parameter memory in which typical characteristics of such living beings, or characteristics of the individual living being to be treated, are stored in advance. In this case, the electrostimulation appliance can also be designed without a measuring appliance and in particular without feedback of measured signals in the sense of a control circuit.

The electrostimulation appliance can also have a measuring appliance with one or more sensors by means of which characteristics of the respiratory cycles of the living being are detected at certain times or continuously and are supplied to the control device. In this case, the characteristics can be stored at least temporarily in the control device. Moreover, additional characteristics of respiratory cycles, defined in advance in the control device, can be stored in a parameter memory, as described above.

The control device can be designed in particular as an electronic control device which has a computer by which the individual functions of the electrostimulation appliance are controlled. In the control device, a computer program can be stored in which the corresponding functions are programmed such that the computer executes the computer program.

Where a computer is mentioned, the latter can be configured to execute a computer program, e.g. in the sense of software. The computer can be designed as a conventional computer, e.g. as a PC, laptop, notebook, tablet or smartphone, or as a microprocessor, microcontroller or FPGA, or as a combination of such elements.

Where regulation is mentioned, regulation differs from control in the sense that regulation involves feedback of measured or internal values, by which the generated output values of the regulation are in turn influenced in the sense of a closed-loop control circuit. In the case of control, a variable is purely controlled without such feedback.

Where the expression "depth of respiration" is used, this expression comprises the actual depth of respiration and also the apparent depth of respiration of the living being. The actual depth of respiration is defined by the size of the tidal volume which is actually exchanged with the environment during exhalation. The tidal volume is the amount of air which is inhaled and exhaled, i.e. ventilated, per breath. The apparent depth of respiration is defined by the size of the tidal volume which, on account of the movement of the respiratory muscles, would be expected to occur if the respiration were able to be performed unimpeded. In many cases, the apparent depth of respiration will correspond to the actual depth of respiration. However, if the airways are completely or partially blocked for example, and/or if the lungs show pathological changes, the actual depth of respiration may also deviate considerably from the apparent depth of respiration.

The actual depth of respiration of the living being can be detected on the basis of different variables, e.g. on the basis of the tidal volume and/or the amplitude of the transpulmonary pressure (TPP). The level of the tidal volume depends on the level of the transpulmonary pressure. The transpulmonary pressure is the pressure difference between the air-filled space of the lungs and the pressure at the outer margin of the lungs between the two pleural membranes. It is therefore the difference between intrapulmonary and intrapleural pressure or, to put it another way, it is the difference between the alveolar pressure and the pleural pressure. The alveolar pressure can only be detected indirectly via measurements in the airways or in a ventilation system. The pleural pressure corresponds approximately to the pressure in the oesophagus. The transpulmonary pressure can, for example, be determined by measurements of the pressures in the ventilation system and in the oesophagus of the living being. The transpulmonary pressure is then the difference ventilation pressure minus oesophageal pressure.

The apparent depth of respiration can be detected on the basis of different variables, e.g. by detecting the movement of the living being, for example movement in the chest region and/or abdominal region, triggered by muscle contraction. Another possibility of detecting or characterizing the apparent depth of respiration is to determine the necessary electrical and/or mechanical energy or force for generating respiratory movements of the living being, which energy or force is necessary for generating a volumetric flow of the respiration. The apparent depth of respiration can therefore be at least approximately determined on the basis of the strength of the stimulation signals output by the at least one signal output device.

The volumetric flow of the respiration indicates how much air volume is actually inhaled or exhaled by the living being per unit of time. A respiratory cycle comprises an inhalation phase (also called inhalation or inspiration for short) and, directly thereafter, an exhalation phase (also called exhalation or expiration for short). At the end of an inhalation at rest, there is still a possible lung volume that could still be inhaled, the inspiratory reserve volume (IRV). At the end of an exhalation at rest, there is still a possible lung volume that could still be exhaled, the expiratory reserve volume (ERV). The respiration at rest thus takes place in a defined respiratory state between inspiratory and expiratory reserve volume (FIGS. 3 and 4).

If the exhalation during respiration at rest is at least partially prevented at each respiratory cycle, the respiratory state shifts to inhalation. Here, the expiratory reserve volume is increased and the inspiratory reserve volume is reduced (FIG. 5). Such a shift of the respiratory state through prevention of exhalation takes place 1. by slowing down the respiratory flow during exhalation, and/or 2. by keeping the exhalation at a defined level, and/or 3. by shortening the exhalation time.

The functions described below, which are performed by the control device, can for example be designed as functions of a computer program or computer programs or computer program modules. If the functions are performed by the control device, the latter can perform the corresponding functions automatically. A large number of functions of the electrostimulation appliance can also be set and/or controlled manually by the user. This also includes functions that can optionally be performed by the control device.

The invention therefore also relates to methods for stimulating one or more nerves and/or muscles of a living being with electrically, electromagnetically and/or magnetically generated stimulation signals by means of such an electrostimulation appliance in which the stated functions are performed manually, for example the modification of the strength of the stimulation signals output by the at least one signal output device, and also a computer program for performing such a method.

With regard to respiratory monitoring, feedback and control, the following can additionally be provided.

For stimulation control, various monitoring parameters and feedback mechanisms can be used. For this purpose, similarly to conventional ventilation, it is possible to detect one, several or all of the parameters of the gas exchange of the living being, such as oxygen uptake and carbon dioxide release, and respiratory parameters such as respiratory impulse, respiratory frequency, tidal volume, speed of respiration, level of exhalation and inhalation. The monitoring can also differentiate thoracic and abdominal breathing and detect them separately.

A particular role, both for the adjustment during the stimulation and also for the effects achieved after the stimulation, is played by parameters that indicate transitions between intensified and relaxed respiration and thus indicate an increase of the respiratory drive. These include, for example, the quotient of respiratory frequency and tidal volume (RSB or rapid shallow breathing index), the P0.1 value, the respiratory flow strength (quotient of tidal volume and inspiration time) and pressure fluctuations in the oesophagus in a defined range of, for example, 4 to 8 mbar, or the extent of pressure fluctuations across the diaphragm.

In addition, the spontaneous electrical activity of the phrenic nerve can also be detected with an electroneurogram (ENG), e.g. likewise electromagnetically, and used for feedback. The electrical spontaneous activity of the phrenic nerve represents a direct measure of the central neural respiratory activity and can be detected, for example, via the number of impulses per breath, the impulse frequency during the inspiratory peak flow, or the average activity over 0.1 second, and used for feedback and for control of the stimulation.

Certain electromyographic patterns can also point to the onset of fatigue. To be able to use electromyographic signals of the diaphragm as a direct measure of the electrical muscle activity for feedback and control of an electromagnetic or electrical respiration, electromyography of the spontaneous activity can take place in the pauses between stimulations. By contrast, artefacts caused by the electromagnetic stimulation can make a measurement difficult or impossible. Here, special stimulation algorithms can permit artefact-free detection of the muscle activity at fixed intervals, which can then be used to control the further stimulation. This control takes account of the fact that the spontaneous activity is neither too low nor too high, e.g. does not exceed 8% of the maximum activity. Furthermore, appliances coupled directly to one another can also permit filtering of the electromagnetic signals. For example, electromyographic monitoring of the achieved muscle activity can also take place during the stimulation, thereby permitting direct feedback.

The relationship between electrical stimulation and the resulting mechanical muscle activity depends on the force-length and force-speed ratio and thus on the thorax volume and shape, but also on the pathological course. For example, in the course of the disease, the diaphragmatic force may decrease, even though the electrical muscle stimulation increases. Therefore, monitoring of the diaphragmatic force is advantageous in particular for the feedback for controlling the training stimulations. Besides indirect parameters such as RSB and the P0.1 value, ultrasound measurements of movements and thickening of the diaphragm can provide an indirect indication of the diaphragmatic force. In the standard method that has been used for many years, the diaphragmatic force is detected indirectly via pressure fluctuations between thoracic space and abdominal space. The phrenic nerve is stimulated with an electromagnetic standard stimulus, and the resulting transdiaphragmatic pressure fluctuations are measured via a balloon catheter in the oesophagus and stomach. The diaphragmatic force can be determined from this.

Further advantageous functions and method steps are explained in detail below.

Group 1: Lung-dependent stimulations

1. Lung-sparing stimulation for a low energy transfer
2. Recruitment and stabilization stimulation for opening collapsed lung areas and maintaining opened regions
3. Lung-protective stimulation for controlling the tidal volume Group 2: Breathing-related stimulations 4. Control stimulation for controlling harmful autonomous respiration
5. Modulation stimulation for modifying the spontaneous respiration Group 3: Conditioning and training stimulations 6. Conditioning stimulation for practicing an improved breathing pattern
7. Training stimulation for training the respiratory muscles Group 1: Lung-Dependent Stimulations Lung-Sparing Stimulation—Stimulation Method 1

Gentle and especially low-energy respiration is achieved by a pattern with a graduated increase in the stimulation strength of the impulses during inhalation and a decrease in the stimulation strength of the impulses during exhalation. In this way, sudden respiratory movements are avoided, thereby minimizing the energy transfer to the lung tissue and the lung injury caused by the respiration itself. The principle is based on the breathing pattern of the newly developed flow-controlled ventilation (FCV) (3) (see also PCT/EP2017/052001).

In this flow-controlled form of ventilation, the conflict between lung-sparing and diaphragm-sparing ventilation is very pronounced, since during FCV spontaneous respiration ought not to be possible. Stimulation method 1, however, can be synchronized with FCV. Such synchronization between electromagnetic or electrical stimulation and FCV can promote a simultaneous autonomous respiration and thus the preservation of the respiratory muscles and their muscle strength in FCV.

During natural spontaneous respiration, the diaphragm is also active during exhalation. With this activity called expiratory braking, the exhalation is braked and the lungs stabilized. This natural activity of the diaphragm during exhalation decreases as the expiratory resistance increases. With this lung-sparing stimulation, a stimulation of decreasing intensity is likewise provided during the exhalation phase. A complete exhalation is only very short or is avoided altogether (see stabilization stimulation under Stimulation method 2). This counteracts a collapse of the lung tissue. In this way, it is possible to prevent not only a disturbance in gas exchange but also an increasing respiratory insufficiency with increased respiratory drive and a damaging spontaneous respiration pattern.

In addition, as a result of the conditioning effect of this form of stimulation, this gentle breathing pattern is trained (see conditioning stimulation under Stimulation method 6). Moreover, both the muscle strength and the muscle mass of the respiratory muscles are maintained and trained, which is of great importance particularly during conventional ventilation and especially during flow-controlled ventilation (FCV) (see training stimulation under Stimulation method 7.1.).

Recruitment and Stabilization Stimulation—Stimulation Method 2

Stimulation method 2 causes occasional, deep sighs in combination with prevention and/or slowing down (see above) of exhalation. This stimulation method recruits collapsed lung areas and stabilizes the lungs by preventing and/or delaying the exhalation. Renewed collapse is prevented in this way.

In recruitment stimulation, it is possible to set not only the depth of inhalation but also the duration of the inhalation phase and also of the exhalation phase. Thus, to increase efficiency in recruitment stimulation, the breathing time ratio can be changed and the time of the maximum inhalation can be lengthened and the time of the exhalation shortened.

In the stabilization stimulation, the end of the exhalation can be held, according to requirements, at different levels by direct stimulation of the respiratory muscles (expiratory hold). As is described under Stimulation method 1, the speed of the exhalation can additionally be slowed down, for example by decreasing the intensity of the stimulation impulses during exhalation, similarly to the abovementioned, natural expiratory braking. The collapse of lung areas can additionally be prevented likewise by changing the breathing time ratio. By changing the stimulation times in the stabilization stimulation, it is possible, as has been described above for the recruitment stabilization, to lengthen the inhalation time and shorten the exhalation phase. If a stimulation in the exhalation phase is not possible or is possible only to an insufficient extent, a complete exhalation can also be prevented (expiratory cut) by earlier initiation of the electromagnetic or electrical stimulation of the inhalation. Here, as has already been mentioned above, precise monitoring of the respiration and in particular of the respiratory state is advantageous, in order to be able to precisely establish the correct time for the inhalation.

In addition, the stabilization stimulation can also be combined with an optionally dynamically adapted increase of the exhalation resistance, as a result of which the exhalation is also slowed down further and the lungs can thus be additionally stabilized in the exhalation phase. This can take place in combination and synchronously with the stimulation during exhalation. During spontaneous exhalation, an increase in the exhalation resistance is thus effected quite naturally by the vocal folds, which open again during inhalation. Through the increase in the exhalation resistance, the natural diaphragmatic activity for the expiratory braking decreases.

This stimulation method 2 also counteracts an increase in respiratory work and respiratory drive, caused by increased lung collapse, and prevents associated further lung injury by self-damaging spontaneous respiration (see also Control stimulation on next page). The recruitment and stabilization stimulation can therefore indirectly reduce or even prevent an increase in respiratory work and harmful respiratory efforts, but also ventilation with high tidal volumes.

Lung-Protective Stimulation—Stimulation Method 3

With the stimulation during inhalation, the depth of respiration is regulated such that a gentle tidal volume of for example 6 ml/kg ideal weight is breathed and/or a transpulmonary pressure of 5 mbar is not exceeded. For this purpose, a feedback can take place between the measurement of the tidal volume, the transpulmonary pressure or corresponding correlates and the stimulation intensity, such that the stimulation can be adapted to the achieved tidal volume and/or the transpulmonary pressure. This then takes place not only for the subsequent breath but instead, by monitoring and feedback, can already directly control the ongoing stimulation. Thus, the ongoing stimulation intensity can be attenuated and/or the stimulation duration can be shortened, so that a defined tidal volume of for example 6 ml/kg ideal weight and/or a transpulmonary pressure of 5 mbar is not exceeded. This is of great importance in particular during spontaneous respiration (see Control and modulation stimulation, Stimulation methods 4 and 5).

Furthermore, sufficient ventilation also has to be ensured in pathological states with high levels of carbon dioxide exhalation. Besides the recruitment and maintenance of gas exchange surface and the level of the tidal volume, this is achieved through a suitably adapted respiratory frequency. The respiratory frequency is defined not only by the incidence of the stimulations but also by the above-described ratio between inhalation and exhalation, the breathing time ratio, which can be set by corresponding stimulation times.

Group 2: Breathing-Related Stimulations Control Stimulation—Stimulation Method 4

Independently of the spontaneous respiration, this electromagnetic or electrical stimulation method achieves a controlled autonomous respiration that is gentler on the lungs, even when the spontaneous respiration follows a completely different, possibly even harmful pattern. Thus, the stimulation can provide targeted counter-control if, for example in the event of excessive respiratory work and increasing fatigue the respiratory drive and respiratory efforts increase. Here, an intensified, rapid and deeper respiration causes damage to an already injured lung and also the already weakened and likewise previously injured respiratory muscles. This increasing lung damage but also diaphragm damage as a result of self-damaging spontaneous respiration is referred to as patient-self inflicted lung injury (P-SILO.

With this stimulation method, the autonomous respiration can be controlled such that overloading of the respiratory muscles and a P-SILT can be reduced or even prevented. The electromagnetic or electrical stimulation is hitherto the only method with which the autonomous respiration can be controlled and thus also optimized non-invasively and without medicaments, independently of the spontaneous respiration and the patient's will.

To control this stimulation method, feedback mechanisms can be used which take account of important features of the spontaneous respiration and/or also of the autonomous respiration ultimately taking place together with the stimulation. Here, tidal volume, transpulmonary pressures, respiratory frequency, respiratory state and indirect characteristics of the respiratory drive are especially of importance for being able to adapt the stimulation individually and flexibly.

Special Form of Control Stimulation: Secretion Mobilization and Coughing

These two methods of stimulation of the respiratory muscles likewise take place independently of the spontaneous respiration and satisfy breath-independent special functions. In this way, secretions are intended to be mobilized from the peripheral to the central airways and to be further mobilized by coughing and, finally, removed from the airways.

Secretion mobilization stimulation: With this stimulation method, secretions can be mobilized from the peripheral to the central airways, e.g. by high-frequency, short and rapid forced exhalations.

Cough stimulation: This stimulation method can take place directly after the secretion mobilization in order to further effectively mobilize mobilized secretions and above all to be able to "cough them out". For this purpose, after a fairly long inhalation, there is a short cough or a series of short coughs. The forced exhalation is more effective if, as in the case of natural coughing, the start of the exhalation takes place against an increased airway resistance and thus the pressure in the lungs can be increased. This short, synchronized increase of the exhalation resistance can be achieved via a synchronized artificial resistance and/or via a narrowing of the vocal folds caused by stimulation of the laryngeal nerves.

Modulation Stimulation—Stimulation Method 5

In contrast to the control stimulation (see Stimulation method 4 above), the modulation stimulation does not take place independently of the spontaneous respiration, but instead as a function of the spontaneous respiration impulse. Instead of the autonomous respiration being controlled entirely independently of the spontaneous respiration, there is therefore a partial or complete control of the natural spontaneous respiration, in which the spontaneous respiration pulse is always taken into account, even if the respiration impulse is only weak or not even present.

Forms of Synchronization

The spontaneous respiration impulse must therefore be detected such that an electromagnetic or electrical stimulation synchronized therewith can take place. The modulation stimulation can be synchronized with the aid of the standard detection methods for the spontaneous respiration pulse, such as fluctuations in pressure, flow or temperature in the air stream or body sensors such as Graseby capsules or muscle activity sensors. Much more exact, however, is the synchronization with the actual nerve impulse before the spontaneous inhalation starts: A ventilation synchronized with the nerve impulse is referred to as neurally assisted or as neurally adjusted ventilatory assist (NAVA). The nerve impulse is detected here via a sensor in the oesophagus in proximity to the diaphragm (4).

However, the actual nerve impulse can also be detected by non-invasive electromagnetic means. This can either take place peripherally, directly over the simulation site on the neck, or centrally, at the site of origin of the nerve impulse in the brain stem region.

Modulation of the Exhalation Level

The spontaneous breaths can then be changed in synchronization with the modulation stimulation as in the above-described Stimulation methods 1 to 3. This can be done by a stimulation over the entire respiratory cycle, as in the lung-sparing stimulation, in order to achieve a gentler spontaneous respiration. Depending on the disease and spontaneous respiration pattern, the modulating stimulation as described under Stimulation method 2 can also only take place in the exhalation phase, in order to stabilize the lungs at different levels by prevention of exhalation and/or delay of exhalation.

Modulation of the Tidal Volume

However, according to requirements, it is also possible for stimulation to be provided in synchronization only in the inhalation phase such that, as described under Stimulation method 2, collapsed lung areas can be re-opened by intermittent, very deep and sustained breaths. Moreover, in cases of insufficient, shallow breathing, the stimulation during the spontaneous inhalation can also permit a sufficient depth of the respiration with a corresponding tidal volume. For this purpose, besides detecting the respiration impulse as also described in the lung-protective stimulation (see Stimulation method 3 above), feedback to the respiration volumes and/or the transpulmonary pressure is also advantageous here.

Moreover, by “taking over” or inhibiting the spontaneous nerve impulse, it is possible to prevent too deep a breath with a lung-damaging excessive tidal volume. Such a take-over can be effected by targeted stimulation of the phrenic nerve directly before the natural nerve impulse, such that the natural impulse cannot be transmitted during the absolute refractory period of the nerve and can be transmitted only in attenuated form in the relative refractory period.

As has already been mentioned above, an excessive spontaneously breathed tidal volume can also be indirectly avoided by prevention of exhalation with shifting of the respiratory state to inhalation. The feedback mechanisms with measurement of the tidal volumes, as described above in the lung-protective stimulation (Stimulation method 3), are likewise used here.

Modulation of Respiratory Frequency

In the previous stimulation forms of modulation stimulation, the spontaneous respiratory frequency was not changed. However, if the frequency of the spontaneous respiration is too fast or too slow, it can be directly and/or indirectly influenced and controlled by the electromagnetic or electrical stimulation. The resulting smooth transitions to controlled autonomous respiration are regulated by detecting the spontaneous respiratory frequency and corresponding feedback mechanisms.

Thus, the extent and the incidence of the stimulation can be individually adapted according to the depth and incidence of the spontaneous respiration. Too fast a spontaneous respiration frequency is indirectly slowed down by lengthened inhalation and/or exhalation phases and, finally, a lower frequency can be superimposed. The respiratory frequency can also be slowed down indirectly by individual deep breaths via the activated respiratory reflexes.

Similarly to conventional back-up ventilation, if breathing is too slow or halting, the respiratory frequency is directly increased with electromagnetically or electrically controlled autonomous respiration. If the breathing decreases slowly, e.g. as the depth of a coma increases, a sufficient respiratory frequency can be achieved early on by a corresponding stimulation frequency, even before an insufficient gas exchange with oxygen deficiency through intermittent breathing occurs.

Modulation Depending on the Intra-Abdominal Pressures

The pressure in the abdominal cavity (intra-abdominal pressure IAP) is increased by inhalation and reduced by exhalation. Thus, as in the case of spontaneous respiration, natural pressure differences between thoracic space and abdominal space occur. The stimulations of the respiratory muscles can bring about natural but also intensified pressure fluctuations in the abdominal cavity which influence the functions of the abdominal organs, e.g. intestinal motility, organ blood supply or lymph drainage, and contribute decisively to the prognosis of ventilated patients.

Thus, as a function of existing intra-abdominal pressures influenced by respiration, the stimulation can control in a targeted manner the depth and the duration of the inhalation but also the level and the duration of the exhalation. If the intra-abdominal pressure, for example at an intra-abdominal hypertension (IAP>12 mbar), is so elevated that blood circulation in the abdominal organs is impaired, the stimulation can accordingly be reduced particularly in the exhalation.

Group 3: Conditioning and Training Stimulations

Conditioning Stimulation—Stimulation Method 6

All of the aforementioned 5 stimulation methods can also be used exclusively as conditioning of an improved spontaneous respiration. Here, an intermittent stimulation takes place with a varying stimulation duration, where only a few breaths may also be sufficient. The conditioning stimulation trains a defined spontaneous respiration pattern, either with a modulation of the spontaneous autonomous respiration or as controlled autonomous respiration with the above-described Stimulation methods 1 to 5.

The conditioning stimulation can be controlled and intensified by direct feedback. The feedback takes place on the basis of detected measured values of the autonomous respiration. The nature of the respiration, the level of the exhalation, the depth of inhalation, the tidal volume and the respiratory frequency are measured, and an accordingly adapted conditioning stimulation is carried out.

A redistribution of the respiratory activity, as arises in positive-pressure ventilation, into the region of the muscles of respiration is thereby prevented. Fatigue or even a decline of the autonomous respiratory activity under conventional ventilation is also avoided, since the peripheral nerve activity with the corresponding afferent impulses from the respiratory muscles can be maintained by the stimulation.

In the “pauses” without conditioning stimulation, spontaneous respiration can take place as normal. However, conventional ventilation can also be provided, or spontaneous respiration assisted by electromagnetic or electrical stimulation can take place, and once again, also in contrast to the conditioning stimulation, autonomous respirations can be modulated as described above. In these pauses, a check is made to ascertain whether, to what extent and especially how long the conditioning stimulation has influenced the spontaneous autonomous respiration. Depending on the changes effected, it is then possible to individually adapt the nature, incidence, duration and above all the interval of the conditioning stimulation via feedback mechanisms.

The conditioning respiration effected by the conditioning stimulation must, like the training stimulation described below, meet certain requirements (see below).

Training Stimulation—Stimulation Method 7

Muscle degradation begins after just a few hours during positive-pressure ventilation, and muscle strength declines even earlier and very quickly. Thus, in muscle biopsies taken after only two hours of ventilation, a reduction in strength of the isolated muscle fibres of ca. 35% was demonstrated (5).

Muscle degradation and weakening of muscle strength are additionally aggravated by the severe disease process, in particular on account of inflammation. If the weakened muscles are only inadequately relieved by ventilation, an increased respiratory drive develops, with a high or ultimately too high respiratory effort, which further weakens and damages not only an already injured lung but also the muscles. The high level of respiratory effort represents the most important factor for injury to the muscles of the diaphragm. The degree between too little respiratory effort and too high a level of respiratory effort can be very narrow and can also differ a great deal between and within individuals. As a result of reduced strength and of muscle degradation, the weakened respiratory muscles are finally no longer able to ensure sufficient autonomous respiration. Respiratory insufficiency develops, with the respiration pattern already described above. Breathing becomes rapid, shallow and intense, which causes further damage to an already injured lung but also to the respiratory muscles. Ventilation withdrawal, which takes up the greatest part of the overall ventilation period, is accordingly critically determined by the recovery of a muscle force adequate for sufficient spontaneous respiration, together with the required rebuilding of muscle mass.

The electromagnetically or electrically stimulated training methods described below are intended to strengthen the respiratory muscles such that muscles can be built up and such that the reduced strength of the existing muscles and muscle degradation can be prevented. Here, further injury to the lungs and respiratory muscles is to be minimized or is to be avoided as far as possible.

Therapeutic, Preventive and Pre-Emptive Forms of Training

By means of electromagnetic or electrical stimulation, the respiratory muscles can be trained such that 1. degraded respiratory muscles are built up again or wreaked muscles are strengthened again, 2. muscle degradation or muscle weakening is prevented, and/or 3. muscles are built up before an expected degradation or strengthening takes place before an expected reduction in strength.

Accordingly, training can be therapeutic, preventive and/or pre-emptive:

1. After degradation and/or weakening of the respiratory muscles through conventional ventilation and the disease process, therapeutic training stimulation takes place in order to rebuild muscles and/or to restore muscle strength.
2. During the conventional ventilation and the disease process, muscle degradation and/or strength reduction is counteracted by preventive training stimulation.
3. Before an expected load increase and/or an expected degradation or weakening of the respiratory muscles through conventional ventilation or the disease process, respiratory muscles and/or muscle strength are built up by the pre-emptive training stimulation.

Intensity of the Training Stimulation

Since the electromagnetic or electrical stimulation provides sufficient ventilation (1), it is assumed that this stimulation intensity in the inhalation is also suitable for preventing muscle degradation, just as normal spontaneous respiration also prevents muscle degradation and loss of strength. In many cases, a lower stimulation intensity is also suitable for preventing muscle degradation, if it is used suitably often for example during conventional ventilation. With more intensive stimulation, respiratory muscles and/or muscle strength can accordingly be built up, or muscle degradation and/or loss of strength can be prevented more effectively even with fewer stimulations.

For training with high stimulation intensity, particular importance is attached to the stimulation during exhalation (see below).

Smooth Transitions for Training Stimulation Patterns

In the training stimulation there are six smooth transitions between . . .

1. . . . a small number of very intensive and a large number of very weak training stimulations.
2. . . . a partial stimulation and a stimulation taking place over the entire respiratory cycle.
3. . . . a stimulation synchronized with the spontaneous respiration and a stimulation independent thereof.
4. . . . a stimulation preventing muscle degradation or reduction in strength and a stimulation causing muscle build-up or increased strength.
5. . . . a training stimulation and a conditioning stimulation.
6. . . . a training stimulation and a ventilation stimulation.

Requirements for the Training Respiration

The training stimulation results in a corresponding training respiration. Therefore, the training patterns likewise focus on the above-described Stimulation methods 1 to 4 and take into account the relationships that are mentioned there. Accordingly, the respiration effected in the training stimulation is also intended to satisfy the following four requirements:

The training respiration should . . .

1. . . . cause no additional injury or only minimal additional injury to the lungs and respiratory muscles and on the contrary should have a positive influence on them.
2. . . . cause no further adverse effects, e.g. hyperventilation.
3. . . . have no negative impact on the spontaneous respiration and on the contrary should, as far as possible, have a positive influence on it.
4. . . . cause no discomfort or only the slightest possible discomfort.

Electromagnetic or Electrical Training Methods

Therefore, in accordance with the Stimulation methods 1 to 6 described above, there are the following six forms of training stimulation, which also permit intensive training stimulation without harmful respiration:

7.1. Lung-sparing training stimulation
7.2. Intensive training stimulation
7.3. Lung-protective training stimulation
7.4. Training stimulation avoiding self-inflicted injury (P-SILT)
7.5. Modulating training stimulation
7.6. Conditioning training stimulation 7.1. Lung-Sparing Training Stimulation The principle, described in Stimulation method 1, of gentle respiration with low energy transfer to the lung tissue applies also to the training stimulation, even if it only takes place occasionally and after quite long intervals. With this stimulation method, sudden and potentially harmful respiratory movements as described above are avoided by a graduated increase in the stimulation impulses during inhalation and a graduated decrease in the stimulation impulses during exhalation. This is of great importance especially for intensive and frequent training stimulations (see 7.2. below).

7.2. Intensive Training Stimulation

With this method, rapid build-up of muscle or increased strength can be achieved and/or muscle degradation and loss of strength can be effectively prevented with only a small number of intensive stimulations. A decisive aspect of this form of stimulation is that there is only little respiration despite intensive muscle activity of the respiratory muscles. As has been described above under Stimulation method 2, this is achieved by a shifting of the respiratory state to inhalation, with prevention of exhalation. In particular, holding the exhalation at a defined level (expiratory hold) requires increased muscular effort. Without causing intensive respiration, a very intensive training stimulation can therefore take place simultaneously with pronounced contractions of the respiratory muscles both in the inhalation phase and in the exhalation phase.

Here, the "holding of the respiration" both in the inhalation phase and in the exhalation phase can be intensified by suitably prolonged stimulation times in the respective respiratory cycles. At the same time, as a secondary effect, as has been described above under Stimulation method 2, collapsed lung areas are opened and ventilated lung regions are stabilized.

This training method permits very intensive training stimulation of the respiratory muscles, with few side effects and with protection of the lungs. Despite pronounced muscle activity, it is possible to avoid not only self-inflicted injuries (see 7.3-7.5 below) but also hyperventilation with corresponding side effects such as hypocapnia and, as a consequence, dangerous pH shifts.

If stimulation in the exhalation phase is not possible, or if it is possible but inadequate, hyperventilation-associated side effects and fatigue can also be avoided by pauses, which can be controlled via feedbacks. In addition, deep breaths can also be limited mechanically by straps and/or weights but also by increasing the airway resistance, as a result of which the training effect can be further intensified.

As a result of the intensive training stimulation, the duration of use per patient can be greatly reduced, as a result of which an appliance can be made available to several patients at short intervals.

An important aspect of this intensive training is that, despite a pronounced stimulation with correspondingly strong contractions of the respiratory muscles, it does not cause deepened breathing with sudden respiratory movements (see 7.1 above) and/or large tidal volumes (see 7.3 below), and/or high transpulmonary pressures.

7.3. Lung-Protective Training Stimulation

As has been described above under Stimulation method 3, the depth of respiration during inhalation is also regulated in this form of training, such that a gentle tidal volume is breathed and/or a gentle transpulmonary pressure is exerted. This is of great importance especially in the case of frequent training stimulations. By way of the above-described feedback between the measurement of the tidal volume and the stimulation strength, a feedback to the respiratory state can additionally take place as has been described above (see 7.2. above).

The stimulation strength can thus be increased, and yet at the same time a lung-protective tidal volume of for example 6 ml/kg ideal weight and/or a transpulmonary pressure of 5 mbar is not exceeded, even in an intensive training stimulation. As has been described under 7.2 above, it is thus possible, through an interaction between respiratory state and tidal volume, to achieve an intensive training stimulation without harmful respiration.

In addition, it is also possible to a limited extent, by increasing the exhalation resistance, to shift the respiratory state to inhalation and thereby to limit the tidal volume. This can be done in combination and in synchronization with the stimulation during exhalation.

However, even with a low stimulation strength, a high tidal volume can be achieved. Also independently of the respiratory state, the lung-protective stimulation prevents a situation where, even at a low stimulation strength, a harmful respiration with large tidal volumes is caused; this excludes the possibility that, particularly in the case of frequent stimulations, a lung-damaging effect is caused by the training stimulation itself. This is of importance especially in spontaneous respiration, since in this case even a low training stimulation, additionally to spontaneous breathing, can considerably strengthen the autonomous respiration then brought about (see 7.4.-7.5 below).

7.4. Training Stimulation Avoiding Self-Inflicted Injury (P-SILT)

Besides the abovementioned 3 training stimulation patterns, which are intended to minimize or prevent additional injury caused by the ventilation effected during the training, this training pattern is intended to avoid or minimize injury in the presence of spontaneous respiration.

The spontaneous respiration is taken into consideration such that an additional training stimulation does not cause any deep and/or sudden inhalations. This is of importance especially in the case of frequent repetitions and can be achieved in different ways. Either, during the inhalation, there is no stimulation or the stimulation is only such that a defined tidal volume is not exceeded, or the inhalation is accordingly modulated.

In a further pattern, the respiratory state can be shifted to inhalation by the prevention of exhalation as described under Stimulation method 2 and also under point 7.2, such that, in this training, the depth of the spontaneous breaths, and thus also self-injuring respiration, is limited during the exhalation.

Accordingly, the spontaneous respiration and/or the autonomous respiration caused or changed by the stimulation must be detected, such that the stimulation can be individually and flexibly adapted and, if necessary, the spontaneous respiration can be modulated (see 7.5 below).

7.5. Modulating Training Stimulation

Finally, there are smooth transitions with different combinations between a training stimulation and a modulation stimulation, as has been described above under Stimulation method 5. Thus, taking into consideration the disease and the severity of the disease, the stimulation can be individually adapted, such that the requirements of autonomous respiration and also the desired training effect can be fulfilled.

The modulating training stimulation always takes account of the spontaneous respiration and therefore also changes it. Here, stimulation is carried out over the entire respiratory cycle or only in part. In the case of partial stimulation, training is effected only in the inhalation phase, only during the exhalation, or in parts of these respiratory phases. Here, as has been described several times above, the exhalation assumes particular importance in order to be able to provide intensive training and to avoid controlled autonomous respiration that is too deep and also to avoid spontaneous respiration that is too deep during the training. Even with fatigued respiratory muscles along with shallow and rapid breathing, the modulating stimulation can provide training at the same time and, as has been described above under Stimulation method 5, an improved breathing pattern can be achieved. As fatigue increases, intervention should be sought as early as possible in order to relieve the fatigued respiratory muscles. If, in cases of extreme fatigue, relief of the respiratory muscles by ventilation should prove necessary, a preventive training stimulation can limit or even prevent the muscle degradation early on.

7.6. Conditioning Training Stimulation

The conditioning stimulation described above under Stimulation method 6 also represents a form of the training stimulation. However, the aim of the conditioning stimulation is not primarily the training of the respiratory muscles but the "practicing" or conditioning of a defined breathing pattern. If, as a supplement to training of the respiratory muscles, a defined breathing pattern is therefore additionally intended to be conditioned, then a conditioning training stimulation takes place.

Combining Stimulation Functions

Depending on the severity of the disease, the lung injury and the respiratory disturbance, a training stimulation can finally be combined with a conditioning stimulation such that the requirements of a suitably adapted ventilation can also be satisfied. For example, in the event of hypoxemic lung injury in the context of ARDS, the stimulation during the exhalation with the aid of the expiratory hold, braking and cut stimulation patterns (see above and below) can stabilize the lungs, protect the lungs against excessively high tidal volumes, condition the "holding" of the exhalation and at the same time bring about intensive training of the respiratory muscles (see overview of exhalation stimulation).

Overview of Exhalation Stimulation

The stimulation during exhalation is of central importance 1. for lung stabilization, 2. for lung protection, 3. for the conditioning of the spontaneous respiration and also 4. for intensive and yet at the same time gentle training of the respiratory muscles.

1. Lung Stabilization

The stabilizing stimulation prevents a collapse of the lungs with corresponding gas exchange disturbances and furthermore also prevents a harmful collapse recruitment ventilation, a hyperdistention of the ventilated lungs, an increase in respiratory work, respiratory efforts, P-SILT and, finally, fatigue. The stabilization stimulation can take place by three different methods: 1. the expiratory hold, 2. expiratory braking and 3. the expiratory cut, which are also able to be combined:

1. Expiratory Hold: Prevention of Complete Breathing Out by Holding of the Exhalation.
2. Expiratory braking: Slowing of the exhalation by decreasing stimulation intensity.
3. Expiratory cut: Shortening of the exhalation duration.

Finally, the exhalation level is determined in particular by the expiratory hold, but also by the nature of the braking and indirectly by shortening of the exhalation time. In contrast to positive-pressure ventilation, there is no unnatural pressure increase in the lungs here, but there is also no unnatural pressure decrease in the abdominal space as in the case of negative-pressure ventilation.

2. Lung Protection

The more air is held in the exhalation, the more the respiratory state shifts to inhalation and the less deep it is then possible to breathe in again. If shifting of the respiratory state means that it is not possible to breathe in so deeply, then high and therefore damaging tidal volumes cannot be achieved purely mechanically. This affects 1. the spontaneous respiration, 2. the electromagnetically or electrically controlled autonomous respiration, 3. the electromagnetic or electrical training respiration, but also 4. even the conventional ventilation. Thus, even the stimulation in the exhalation itself makes it possible to limit harmful spontaneous respiration, but also harmful electromagnetic or electrical but also conventional ventilation with large tidal volumes.

3. Conditioning

The conditioning stimulation assists the practice of the various exhalation methods in a targeted manner, in order thereby to learn more effectively a defined exhalation technique for the subsequent spontaneous respiration.

4. Training

The stimulation in the exhalation permits intensive training of the respiratory muscles by limiting the inhalation by a shift of the respiratory state. This permits a very intensive training stimulation with pronounced contractions of the respiratory muscles both in the inhalation phase and in the exhalation phase since, despite intensive muscle activity of the respiratory muscles, there is only slight respiration. In this way, it is possible to avoid an extensive training respiration, but also a harmful spontaneous respiration during the training, and the associated harmful effects and complications.

BRIEF DESCRIPTION OF THE DRAWINGS

The invention is explained in more detail below on the basis of illustrative embodiments and with reference to drawings.

In the drawings.

DESCRIPTION OF THE INVENTION

Figure 1:
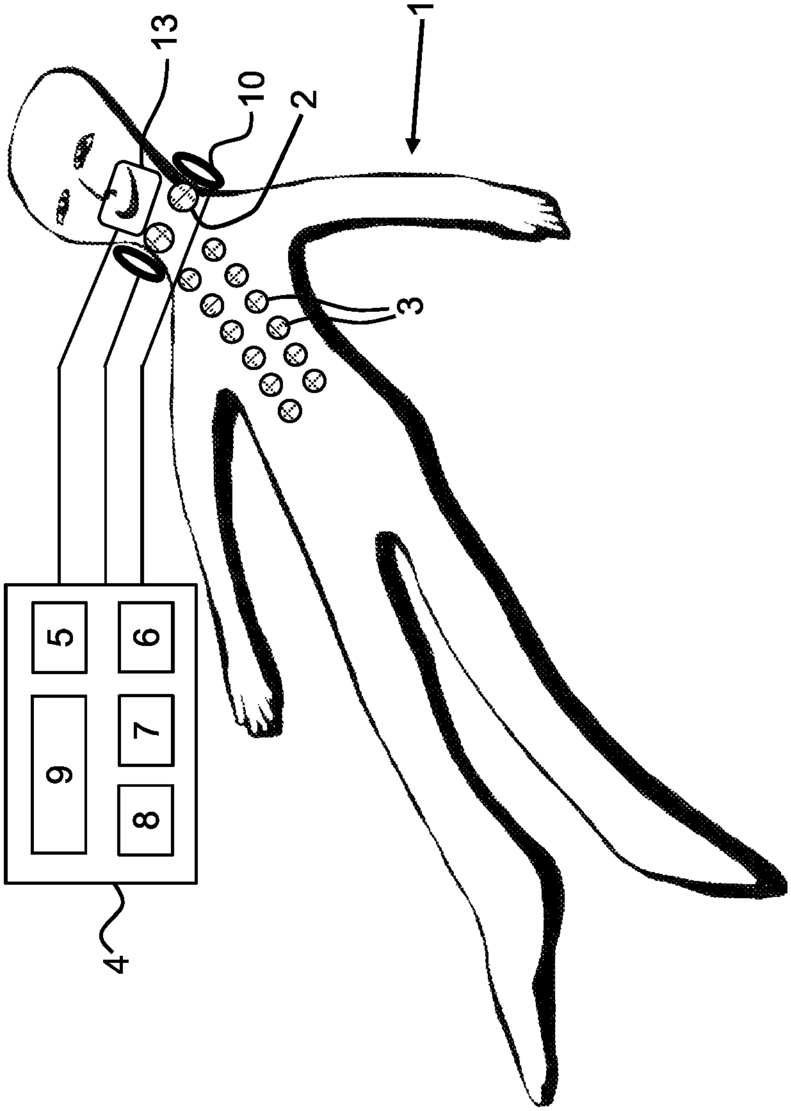
FIG. 1 shows the use of an electrostimulation appliance on a living being.

FIG. 1 shows a living being 1 in a recumbent position. To make matters clear, advantageous stimulation positions of the phrenic nerve 2 and of the intercostal nerves 3 are shown on the living being 1. In the present illustrative embodiment, it is assumed that the phrenic nerve 2 is intended to be stimulated by electromagnetic stimulation.

FIG. 1 shows an electrostimulation appliance 4 which is connected by electrical lines to signal output elements 10, e.g. coils, for feeding magnetic fields into the living being 1. By way of the signal output elements 10, the electrostimulation appliance can generate stimulation signals in the living being, which stimulation signals can generate muscle contractions by which the respiration of the living being 1 can be influenced in a targeted manner.

The electrostimulation appliance 4 can be designed, for example, as a computer-controlled electrostimulation appliance. It has a computer 5, a stimulation signal generator 6, a memory 7 and operating elements 8. A display device for displaying operational data can additionally be present. In the memory 7, a computer program is stored with which some or all of the functions of the electrostimulation appliance 4 can be executed. The computer 5 executes the computer program in the memory 7. In this way, the stimulation signal generator 6 outputs corresponding stimulation signals to the signal output device 10, by which the desired magnetic fields are generated. The above-described functions for the ventilation of the living being 1 by the stimulation signals, or the processes to be carried out by the user, can be influenced by the user via the operating elements 8, e.g. by setting parameters of respiratory cycles.

The artificial ventilation of the living being 1 by electrostimulation can be controlled by the described elements. If certain parameters are also to be regulated, it is necessary that one or more measured values of characteristics of respiratory cycles of the living being 1 are supplied to the electrostimulation appliance 4. For example, it may be expedient to detect the volumetric flow inhaled by the living being 1 and the exhaled volumetric flow. This can be effected, for example, by means of a face mask 13 in which a flow sensor is arranged. The face mask 13 or the flow sensor has practically no influence on the respiratory flow. However, quantitative variables that characterize the volumetric flow can be detected and supplied to the electrostimulation appliance 4. The evaluation of the sensor signals can be effected, for example, by the computer 5.

The electrostimulation appliance 4 can additionally have an interface 9 for connection to other appliances, e.g. for data exchange with other appliances. In this way, further measured values can be supplied to the electrostimulation appliance 4 without the electrostimulation appliance 4 having to be equipped with its own sensors.

Figure 2:
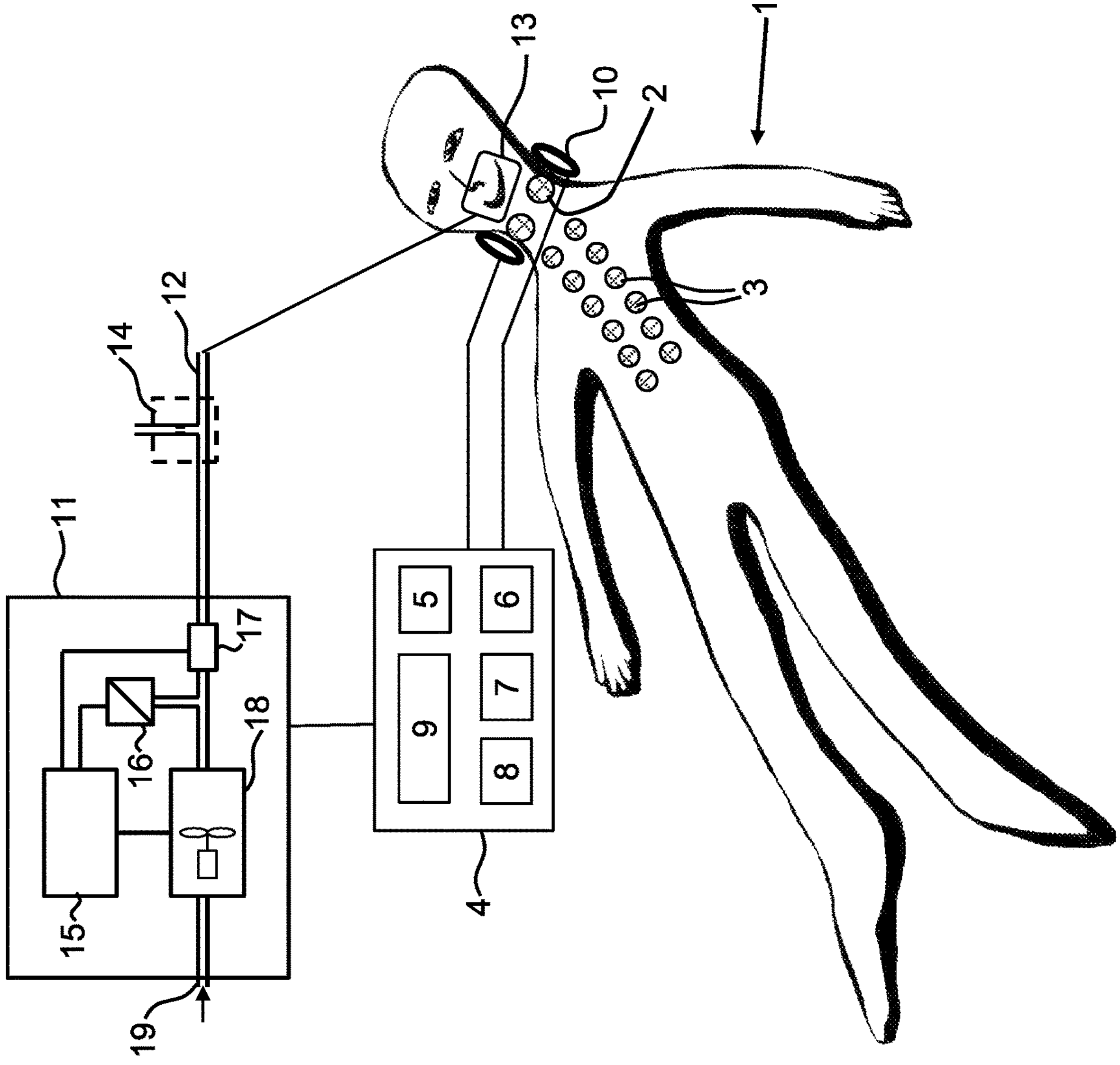
FIG. 2 shows the use of an electrostimulation appliance in conjunction with positive-pressure ventilation on a living being.

FIG. 2 illustrates the use of the electrostimulation appliance 4 on the living being 1 in conjunction with a positive-pressure ventilator 11. The ventilator 11 has an air delivery unit 18 through which air can be suctioned from the environment via a port 19 and can be fed by means of a breathing mask 13 into the airways of the living being 1 via an air line 12. The breathing mask 13 or the air line 12 can have a defined leakage 14. Inside the ventilator 11, a pressure sensor 16 and a volumetric flow sensor 17, e.g. a pneumotachograph, are connected to the air line 12. The ventilator 11 has its own control unit 15, to which the sensors 16, 17 are connected. The control unit 15 actuates the air delivery unit 18 according to predefined algorithms, in order in this way to generate desired volumetric flow curves and/or pressure curves in the organs of respiration of the living being 1 via the breathing mask 13.

It will be seen that the electrostimulation appliance 4 is connected via its interface 9 to the ventilator 11. By way of the interface 9, the corresponding measured values, and optionally additional values calculated internally in the ventilator 11 and concerning characteristics of the respiratory cycles of the living being, are supplied to the electrostimulation appliance 4. In this way, the electrostimulation appliance 4 receives, for example, current measured values of the pressure and of the volumetric flow of the respiratory cycles of the living being 1.

Figure 3:
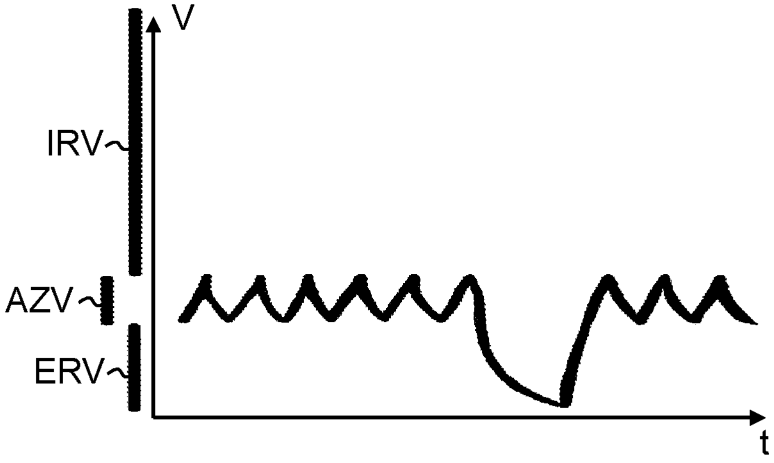
FIGS. 3 to 5 show time diagrams of respiratory states.
Figure 4:
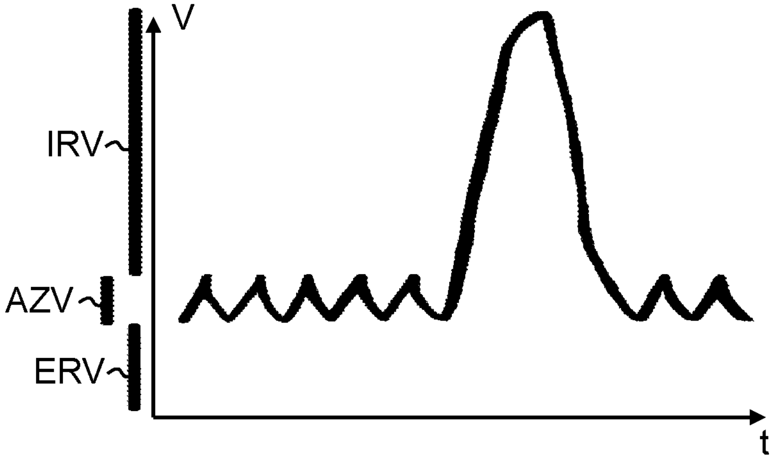
Figure 5:
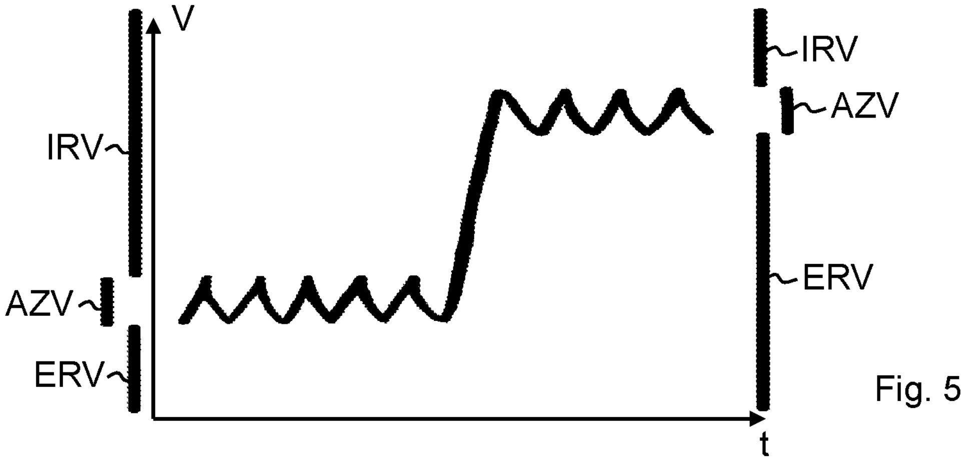

FIGS. 3 to 5 each show several respiratory cycles plotted over time t for various respiratory states. The air volume V located in each case in the lungs is plotted on the ordinate.

FIG. 3 shows the respiratory state with tidal volumes during respiration at rest (AZV) and a maximum possible exhalation, by which the normal respiratory state during respiration at rest and the end-expiratory reserve volume (ERV) are intended to be illustrated. The inspiratory reserve volume (IRV) is also characterized here and is illustrated in FIG. 4 by the maximum possible inhalation. FIG. 5, finally, shows the shift of the respiratory state under respiration at rest into the inhalation, which is characterized in that the tidal volumes of the respiration at rest are at an increased ERV and a reduced IRV.

The respiratory profiles shown in FIGS. 3 to 5 can be suitably controlled or regulated by the electrostimulation appliance 4 according to the invention and the methods according to the invention, i.e. corresponding stimulation signals are fed by the electrostimulation appliance into at least one nerve and/or one muscle of the living being 1, as a result of which the corresponding muscle contractions of the respiratory muscles are generated, which ultimately bring about the illustrated respiratory cycles.

Figure 6:
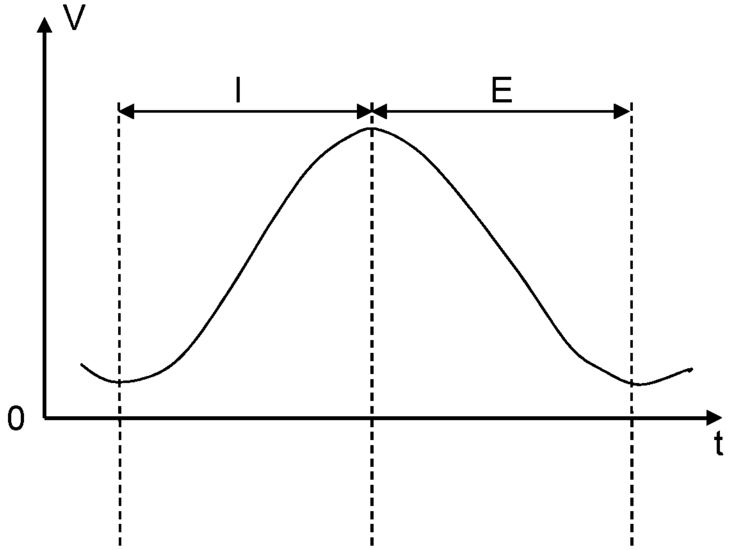
FIG. 6 shows the change of the air volume in the lungs in a respiratory cycle over time.
Figure 7:
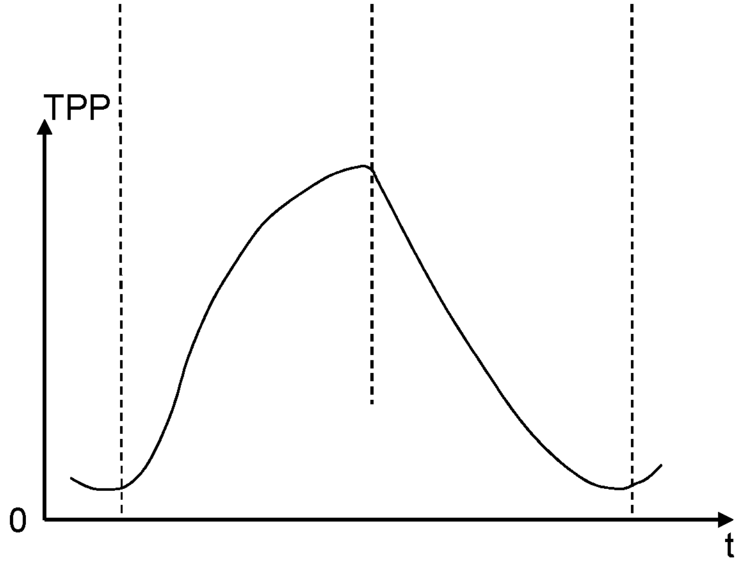
FIG. 7 shows the change of the transpulmonary pressure in a respiratory cycle over time.

FIGS. 6 and 7 show a respiratory cycle in an enlarged view. The respiratory cycle consists of an inspiration phase I and an expiration phase E. FIG. 6 shows the air volume V over time, while FIG. 7 shows the transpulmonary pressure TPP over time. It will be seen that the inspiration phase I according to FIG. 6 begins at the lower vertex and ends at the upper vertex. The expiration phase E begins at the upper vertex and ends at the subsequent lower vertex of the curve. The profile of the pressure TPP is phase-shifted in relation to the profile of the volume V.

The electrostimulation appliance 4 can, for example, generate the profiles of the respiratory cycles shown in FIG. 6 and FIG. 7. According to the selected function, the duration of the inspiration phase and/or the duration of the expiration phase can be influenced separately. The amplitude of the volume profile and/or of the pressure profile can also be influenced separately, and also the respective positions of the maxima and minima of the curve profiles.

What is claimed is:

1. An electrostimulation appliance configured for stimulating one or more nerves and/or muscles of a living being with electrically, electromagnetically and/or magnetically generated stimulation signals, comprising:

a) at least one signal output device through which electrically, electromagnetically and/or magnetically generated stimulation signals can be fed into at least one nerve and/or one muscle;

b) at least one control device which is configured to activate the at least one signal output device in such a way that the stimulation signals output by the at least one signal output device are able to generate muscle contractions in the living being, by which the respiration of the living being can be influenced in a targeted manner, wherein by setting parameters of the stimulation signals output by the at least one signal output device, the control device is configured to control the characteristics of the respiratory cycles to predetermined target characteristics of the respiratory cycles in order to avoid patient self-inflicted lung injury due to spontaneous respiration.

2. The electrostimulation appliance according to claim 1, wherein the control device is configured to modify the strength of the stimulation signals, output by the at least one signal output device, over the course of a respiratory cycle of the living being in several steps and/or uniformly.

3. The electrostimulation appliance according to claim 1, wherein by setting parameters of the stimulation signals output by the at least one signal output device, the control device is configured to control or regulate the respiration of the living being, for a limited time period, to a depth of respiration that is too low for a life-supporting gas exchange of the living being.

4. The electrostimulation appliance according to claim 1, wherein current measured values of characteristics of the respiratory cycle of the living being are determined continuously by at least one sensor and supplied to the control device, wherein, by setting parameters of the stimulation signals output by the at least one signal output device, the control device is configured to regulate the characteristics of the respiratory cycles to predetermined target characteristics of the respiratory cycles, as a function of the measured values.

5. The electrostimulation appliance according to claim 1, wherein current measured values of the spontaneous respiration impulses are determined continuously by at least one spontaneous respiration impulse sensor, which is able to detect the spontaneous respiration impulses of the living being, and are supplied to the control device, wherein the control device is configured to modify parameters of the stimulation signals, output by the at least one signal output device, as a function of the measured values of the spontaneous respiration impulses, in particular in a manner synchronized with the spontaneous respiration impulses.

6. The electrostimulation appliance according to claim 1, wherein by setting parameters of the stimulation signals output by the at least one signal output device, the control device is configured to control or regulate, over a large number of respiratory cycles, the characteristics of the respiratory cycles to predetermined target characteristics of the respiratory cycles, thereafter, over a large number of respiratory cycles, to have no influence on the respiratory cycles of the living being, and thereafter, again over a large number of respiratory cycles, to control or regulate the characteristics of the respiratory cycles to predetermined target characteristics of the respiratory cycles.

7. The electrostimulation appliance according to claim 1, wherein current measured values of the depth of respiration are determined continuously by at least one depth of respiration sensor, which is able to detect measured values of the depth of respiration of the living being, and are supplied to the control device, wherein, by setting parameters of the stimulation signals output by the at least one signal output device, the control device is configured to regulate the respiration of the living being, on the basis of the measured values of the depth of respiration, to a predetermined value, value range and/or temporal change of the depth of respiration.

8. The electrostimulation appliance according to claim 1, wherein by setting parameters of the stimulation signals output by the at least one signal output device, the control device is configured to limit the depth of respiration and/or the volumetric flow in the inspiration phase to a predetermined maximum value.

9. The electrostimulation appliance according to claim 1, wherein by setting parameters of the stimulation signals output by the at least one signal output device, the control device is configured to limit the volumetric flow in the expiration phase to a predetermined maximum value and/or to reduce it in relation to the average intrinsic volumetric flow of the living being in the expiration phase.

10. The electrostimulation appliance according to claim 1, wherein by setting parameters of the stimulation signals output by the at least one signal output device, the control device is configured to reduce the duration of the expiration phase in relation to the average intrinsic duration of the expiration phase of the living being.

11. The electrostimulation appliance according to claim 1, wherein over the course of a respiratory cycle, the control device is configured to increase the strength of the stimulation signals, output by the at least one signal output device, in the inspiration phase and to reduce it again in the expiration phase.

12. The electrostimulation appliance according to claim 1, wherein the control device is configured to variably activate a throughflow control actuator, which is coupled pneumatically and/or electrically to the respiratory system of the living being and by which the volumetric flow of the air stream flowing into and/or flowing out of the living being is adjustable, over the course of a respiratory cycle, in such a way that the volumetric flow in the inspiration phase and/or the expiration phase is at least temporarily limited or reduced by the throughflow control actuator.

13. The electrostimulation appliance according to claim 1, wherein the spontaneous respiration impulse sensor is designed as a nerve impulse sensor which is able to detect nerve impulse signals of the living being that control the respiration of the living being.

14. The electrostimulation appliance according to claim 1, wherein the control device is connectable via an interface to a ventilator which is configured to ventilate the living being by generating variable positive pressure and/or negative pressure, wherein the control device is configured for data exchange with a control device of the ventilator.

15. The electrostimulation appliance according to claim 1, wherein the control device is configured to store characteristics of one or more respiratory cycles of the living being that quantitatively characterize the respective respiratory cycle.

16. The electrostimulation appliance according to claim 1, wherein the control device is configured to initially bring about deep inhalation in the respiratory cycle by suitably adapting the strength of the stimulation signals output by the at least one signal output device.

17. The electrostimulation appliance according to claim 16, wherein subsequent to the deep inhalation, and by setting parameters of the stimulation signals output by the at least one signal output device, the control device is configured to bring about one or more partial exhalations with, compared to the average exhalation, a shortened exhalation duration and/or an increased strength of the stimulation signals.

18. The electrostimulation appliance according to claim 16, wherein by setting parameters of the stimulation signals output by the at least one signal output device, the control device is configured to stimulate secretion mobilization and, subsequent to the stimulation of secretion mobilization, to bring about deep inhalation.

19. The electrostimulation appliance according to claim 1, wherein on the basis of the output stimulation signals, the control device is configured to alternately stimulate purely thoracic breathing, purely abdominal breathing or a combination thereof, wherein the strengths of the stimulation of the abdominal breathing and of the thoracic breathing can be adaptable independently of each other.

* * * * *